(12) United States Patent
Barthelmes et al.

(10) Patent No.: US 11,305,305 B2
(45) Date of Patent: Apr. 19, 2022

(54) METHOD FOR CONTROLLING AN ELECTROSTATIC ATOMIZER FOR LIQUIDS

(71) Applicant: J. Wagner GmbH, Markdorf (DE)

(72) Inventors: Jan Barthelmes, Salem (DE); Alfred Göhring, Salem (DE); Thomas Jeltsch, Friedrichshafen (DE); Holger Stohl, Markdorf (DE); Urban Bischofberger, Berneck (CH)

(73) Assignee: J. Wagner GmbH, Markdorf (DE)

( * ) Notice: Subject to any disclaimer, the term of this patent is extended or adjusted under 35 U.S.C. 154(b) by 77 days.

(21) Appl. No.: 16/657,167

(22) Filed: Oct. 18, 2019

(65) Prior Publication Data

US 2020/0114375 A1 Apr. 16, 2020

Related U.S. Application Data

(63) Continuation of application No. PCT/EP2018/060121, filed on Apr. 19, 2018.

(30) Foreign Application Priority Data

Apr. 21, 2017 (DE) .................... 10 2017 108 614.5

(51) Int. Cl.
*B05B 5/16* (2006.01)
*B05B 5/00* (2006.01)
(Continued)

(52) U.S. Cl.
CPC ............ *B05B 5/1691* (2013.01); *A45D 34/00* (2013.01); *A61M 35/30* (2019.05); *B05B 5/006* (2013.01);
(Continued)

(58) Field of Classification Search
CPC .............................. B05B 5/005; B05B 5/006
See application file for complete search history.

(56) References Cited

U.S. PATENT DOCUMENTS 4,785,995 A * 11/1988 Yamane ............... B05B 3/1057
118/626
10,179,338 B2 1/2019 Dau et al.
(Continued)

FOREIGN PATENT DOCUMENTS

AU  2004203520 B2 * 6/2006 ............... B05B 5/10
DE  1 522 540 A      9/1969
(Continued)

OTHER PUBLICATIONS

JP59-053106, machine translation. (Year: 1984).*
(Continued)

*Primary Examiner* — Robert A Vetere
(74) *Attorney, Agent, or Firm* — Burr & Brown, PLLC

(57) ABSTRACT

The invention relates to a method for controlling an electrostatic atomizer for liquids, the atomizer comprising a liquid tank and a delivery device for liquid from the liquid tank, a high-voltage source and also at least one atomizer nozzle for the atomization of liquid, the at least one atomizer nozzle being connected to the high-voltage source. Here, the voltage and/or the current intensity at at least one of the atomizer nozzles are detected by sensors of control electronics and/or the voltage and/or the current intensity at the high-voltage source are detected by sensors of the control electronics.

14 Claims, 3 Drawing Sheets

(51) Int. Cl.
  *B05B 5/035* (2006.01)
  *B05B 5/053* (2006.01)
  *B05D 1/04* (2006.01)
  *B05B 11/00* (2006.01)
  *A61M 35/00* (2006.01)
  *A45D 34/00* (2006.01)
  *G05B 11/01* (2006.01)

(52) U.S. Cl.
  CPC .............. *B05B 5/035* (2013.01); *B05B 5/053* (2013.01); *B05D 1/04* (2013.01); *G05B 11/013* (2013.01); *A45D 2200/155* (2013.01); *B05B 11/3053* (2013.01)

(56) References Cited

U.S. PATENT DOCUMENTS

| | | | |
|---|---|---|---|
| 2008/0290185 A1* | 11/2008 | Duru | B05B 17/0676 |
| | | | 239/4 |
| 2009/0184186 A1 | 7/2009 | Suda et al. | |
| 2010/0116897 A1 | 5/2010 | Lind et al. | |
| 2011/0040147 A1* | 2/2011 | O'Dea | A61M 15/02 |
| | | | 600/104 |
| 2012/0207651 A1* | 8/2012 | Micheli | A61L 2/22 |
| | | | 422/292 |
| 2017/0136501 A1* | 5/2017 | Rifkin | B08B 1/00 |

FOREIGN PATENT DOCUMENTS

| | | |
|---|---|---|
| EP | 1 504 823 A1 | 2/2005 |
| EP | 3 613 403 A1 | 2/2020 |
| GB | 1143840 A | 2/1969 |
| JP | S58-017864 A1 | 2/1983 |
| JP | 59053106 B * | 12/1984 |
| JP | 2006-007195 A | 1/2006 |
| JP | 2013-027832 A | 2/2013 |
| JP | 2013-094719 A1 | 5/2013 |
| JP | 2015-089537 A | 5/2015 |

OTHER PUBLICATIONS

International Search Report and Written Opinion (Application No. PCT/EP2018/060121) dated Jun. 13, 2018.

European Office Action (Application No. 18719153.1) dated Oct. 13, 2020.

English translation of International Preliminary Report on Patentability (Chapter I) (Application No. PCT/EP2018/060121) dated Oct. 31, 2019, 9 pages.

Japanese Office Action (with English translation), Japanese Application No. 2019-557470, dated Jan. 20, 2022 (6 pages).

* cited by examiner

METHOD FOR CONTROLLING AN ELECTROSTATIC ATOMIZER FOR LIQUIDS

CROSS REFERENCE TO RELATED APPLICATIONS

This application is a continuation of International Application No. PCT/EP2018/060121 filed Apr. 19, 2018, which designated the United States, and claims the benefit under 35 USC § 119(a)-(d) of German Application No. 10 2017 108 614.5 filed Apr. 21, 2017, the entireties of which are incorporated herein by reference.

FIELD OF THE INVENTION

The present invention relates to a method for controlling an electrostatic atomizer for liquids.

BACKGROUND OF THE INVENTION

In the context of the present invention, electrostatic atomization comprises all atomization processes that atomize liquids with effects under the influence of a high voltage. In particular, electrohydrodynamic effects and electrokinetic effects are also covered by the concept of this type of atomization. In the context of the present invention, an electrostatic atomization may also be understood as meaning an electrohydrodynamic atomization.

US 2010/0116897 A1 discloses a method for controlling an electrostatic atomizer for liquids, the atomizer comprising a liquid tank and a delivery device for liquid from the liquid tank, a high-voltage source and also at least one atomizer nozzle for the atomization of liquid, and the at least one atomizer nozzle being connected to the high-voltage source.

The connection of the atomizer nozzle to the high-voltage source should be understood as meaning any kind of interaction that enables the electrostatic, in particular, electrohydrodynamic atomization by the high voltage. An atomizer nozzle may in this case consist of conductive material, but also of non-conductive material, in order to bring about the necessary effects.

SUMMARY OF THE INVENTION

The present invention is based on the object of proposing a method for controlling an electrostatic atomizer for liquids by which a spraying operation can be monitored and improved.

In the case of the method for controlling an electrostatic atomizer for liquids, it is provided that the voltage and/or the current intensity at least one of the atomizer nozzles are detected by sensors of control electronics and/or that the voltage and/or the current intensity at the high-voltage source are detected by sensors of the control electronics. This makes it possible to draw conclusions about the working mode and the working result of the atomizer and to intervene in a directive manner by sensors of the control electronics to improve the spraying result or to avoid errors.

With respect to the advantages of the further claims, reference is made to the description of the figures.

In the context of the present invention, an electrostatic atomization may also be understood as meaning an electrohydrodynamic atomization.

In the context of the present invention, a grid may also be understood as meaning an arrangement of a number of columns arranged next to one another and rows arranged below one another. A triangle symmetry is also conceivable as a grid arrangement.

In the context of the present invention, a liquid should be understood as meaning any kind of liquid suitable for being applied by electrostatic atomization. In the context of the present invention, it is provided, in particular, that the liquid is a cosmetic, for example, a sunscreen, a lotion or a deodorant. The liquid may also be a liquid paint or lacquer or the like. Other liquids, for example, an insect repellent, are also conceivable.

BRIEF DESCRIPTION OF THE DRAWINGS

Further details of the present invention will be described in the drawing with reference to schematically illustrated exemplary embodiments.

DETAILED DESCRIPTION OF THE INVENTION

Figure 1:
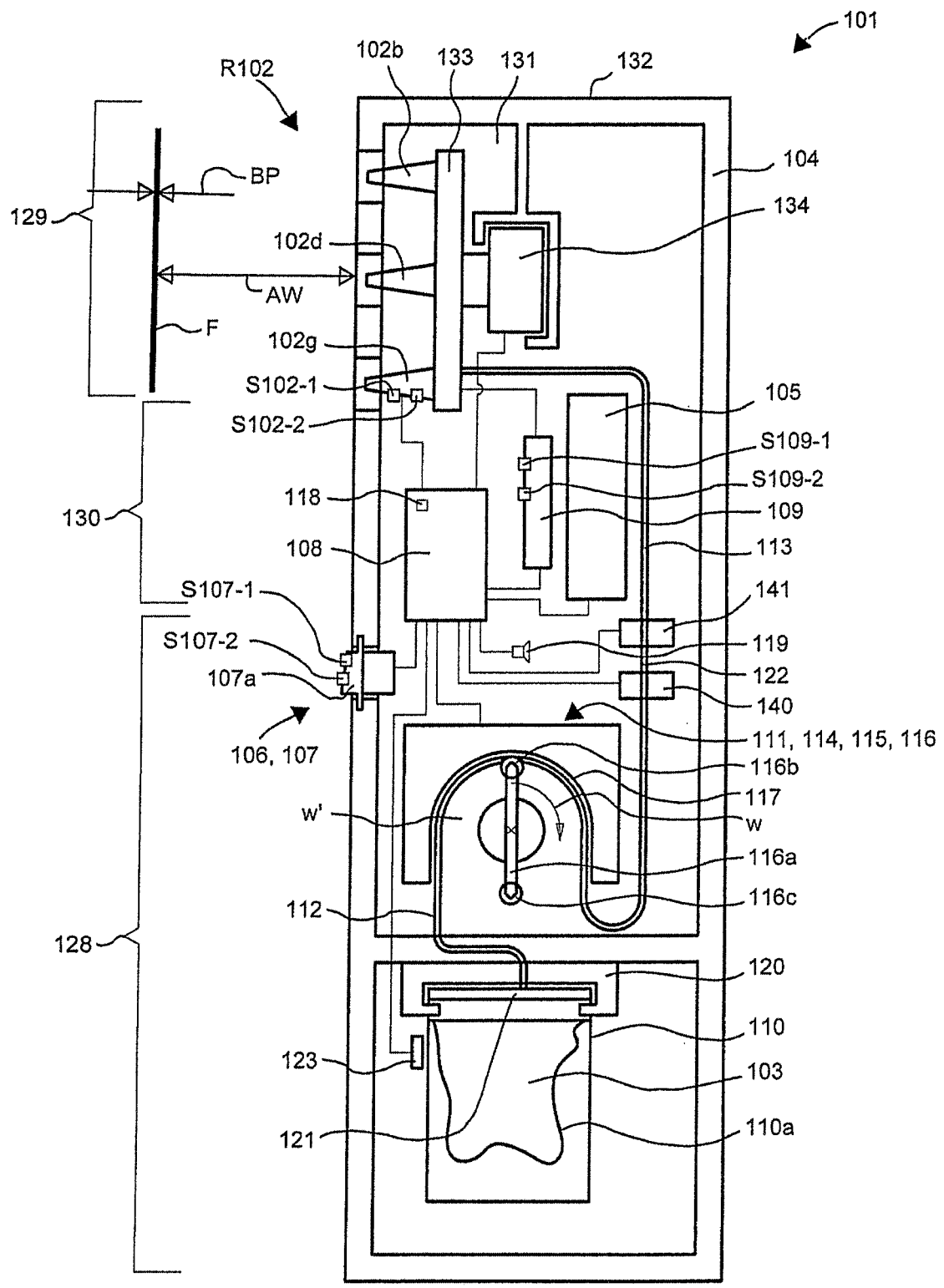
FIG. 1 shows a sectional view through a schematic representation of a first variant of an embodiment of an atomizer, the atomizer nozzles being in an inactive position.
Figure 2:
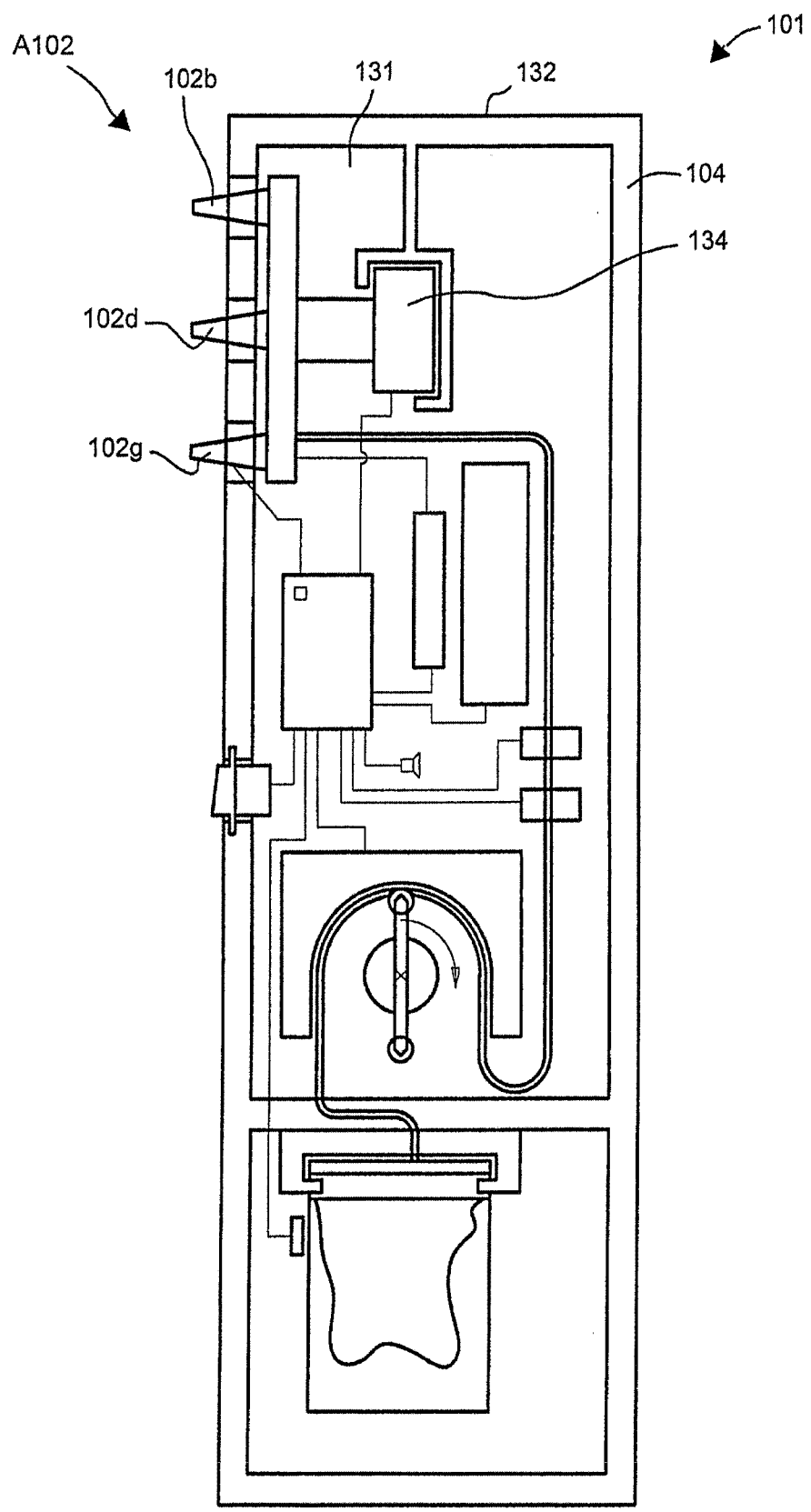
FIG. 2 shows a sectional view through the representation of FIG. 1, the atomizer nozzles being in an active position.
Figure 3:
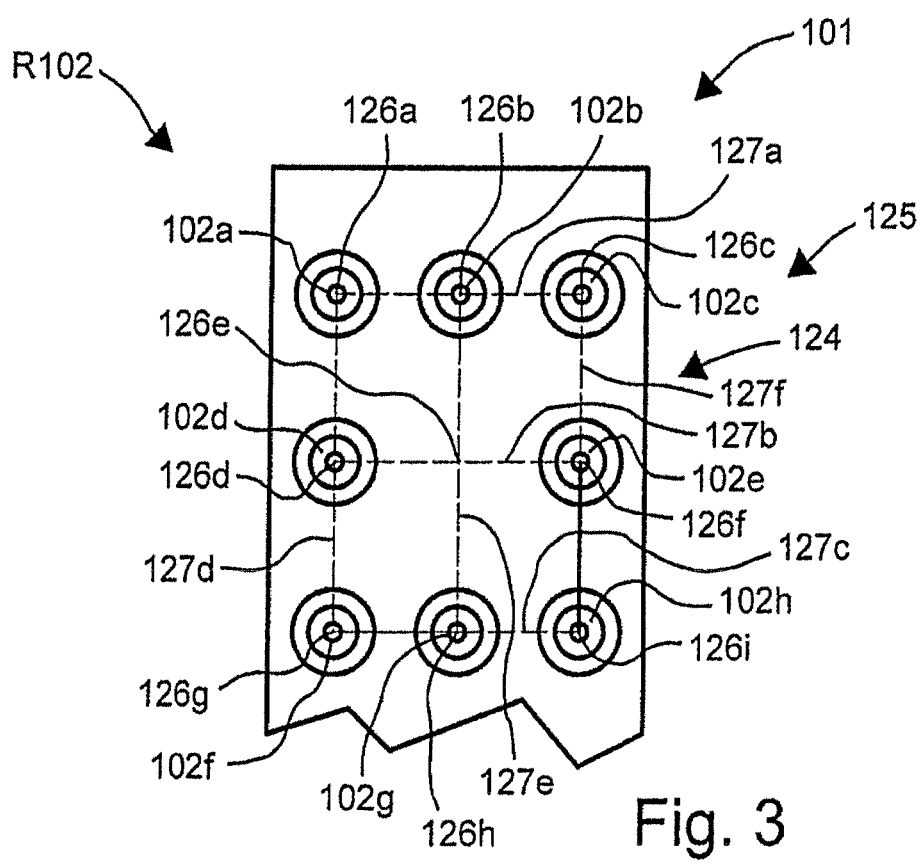
FIG. 3 shows a side view of FIG. 1 in the region of the atomizer nozzles.

In FIG. 1, a sectional view through a schematic representation of an atomizer 101 is shown, with atomizer nozzles 102a to 102h being in an inactive position R102. In FIG. 2, the atomizer 101 shown in FIG. 1, comprising atomizer nozzles 102a to 102h that are in an active position A102, is shown. FIG. 3 finally shows a side view of the atomizer 101 represented in FIG. 1 in the region of its atomizer nozzles 102a to 102h.

The version represented has a multiplicity of atomizer nozzles. It is, however, likewise included according to the present invention and expedient to provide a smaller number of atomizer nozzles, in particular, between two and five atomizer nozzles, depending on which requirements the liquid to be atomized imposes on the geometry and arrangement of the nozzles in connection with the electrostatic effects.

The electrostatic atomizer 101 is intended for an electrostatic atomizer of liquids 103. Liquids are understood here as meaning, in particular, cosmetics, but also, for example, paints and lacquers. The atomizer 101 comprises a housing 104, an electrical energy source 105, an activation mechanism 106, which is designed as an electrical button 107 or an electronic contact (capacitive, dry-reed, Hall sensor), control electronics 108, a high-voltage source 109, a liquid tank 110, a delivery device 111 and the mentioned atomizer nozzles 102a to 102h. The delivery device 111 is arranged between the liquid tank 110 and the atomizer nozzles 102a to 102h. The delivery device 111 is connected here to the liquid tank 110 by a first line 112 and the delivery device 111 is connected here to the atomizer nozzles 102a to 102h by a second line 113, so that during spraying operation the delivery device 111 sucks liquid 103 out of the liquid tank 110 and delivers it to the atomizer nozzles 102a to 102h. Particularly preferably, each atomizer nozzle is connected to the liquid tank via the delivery device by a delivery line of its own. In this case, the delivery lines are formed, in particular, in one piece as extruded plastic hoses, as are known from hose pumps.

The delivery device 111 is formed as a pump 114, specifically a positive displacement pump in the style of a suction pump 115. The suction pump 115 is formed as a hose pump 116 and is designed such that, during pumping operation, a delivery hose 117 arranged between the first line 112 and the second line 113 is alternately deformed in a rolling manner by rollers 116b, 116c arranged on a rotor 116a, and thereby completely pinched, as is shown in FIG. 1 in the region of the roller 116b.

The atomizer 101 comprises a switching device 118, by means of which a direction of rotation of the rotor 116a of the hose pump 116 can be switched over in such a way that the hose pump alternates between a delivery mode, in which the rotor 116a turns in a direction of rotation w, and a return mode, in which the rotor 116a turns in an opposite direction of rotation w'. A short return mode makes it possible to avoid an undesired escape of liquid 103 after spraying.

It is intended here in a refinement to avoid a return of the liquid 103 into the liquid tank 110. Avoiding returns is expedient if the liquid in the tank has to comply with stringent hygiene requirements, and contamination by liquid that has already been removed is to be avoided. This is achieved by the first line 112, which like the delivery hose 117 is formed as elastically expandable, being slightly expanded by the return to increase the size of its inner volume, and the liquid tank 110 remaining closed by a nonreturn valve that is not represented. In order to ensure a great storage volume of the first line for a return, it is envisaged to make the first line at least 1.5 times and, in particular, twice as long as is required for connecting the liquid tank to the delivery device. Alternatively, it is also envisaged to conduct small amounts of liquid via a diverter or a corresponding valve into a disposal tank during the return mode. This makes it possible to empty the second line 113 largely completely.

Alternatively, it is also envisaged to allow returns into the liquid tank through an opened valve. This is of advantage, in particular, whenever the liquid removed, for example, a sunscreen, is to be returned to the liquid tank from the circulation of the atomizer in order to empty the atomizer as completely as possible without wasting material.

The delivery device 101 and the high-voltage source 109 can be activated by way of the activation mechanism 106, which is formed by the electrical button 107. An actuating element 107a of the button 107 is electrically conductive here and is formed as an opposite pole in relation to the atomizer nozzles 102a to 102b. Since the button 107 has to be pressed for a sustained time for spraying, in this way good connection of the user to the reference potential of the spray device 101 is ensured and electrostatic charging of the user is avoided.

The atomizer 101 comprises an acoustic signal transmitter 119, which is connected to the control electronics 108. As a result, the user can be informed acoustically of a correct or incorrect use of the atomizer 101, and the handling of the atomizer 101 can in this way be trained and optimized. Also provided in addition or alternatively is a haptic, in particular, vibrating signal transmitter, this always being active at a specific frequency when the atomizer is spraying. By vibrating at a different frequency, further information, for example, incorrect operation, can be conveyed to the user.

The atomizer 101 comprises a connection mechanism 120, the liquid tank 110 being connected to the connection mechanism 120 releasably and by way of a self-closing valve 121. As a result, a coupling and decoupling of the liquid tank 110 is possible by easy manual movements, and as a result undesired running out from the liquid tank 110 is also effectively prevented.

The liquid tank 110 is formed as a self-collapsing tank, and for this purpose comprises a film bag 110a. Alternatively, the liquid tank may also be equipped with a passive follow-up piston. Such liquid tanks can be produced at low cost. Furthermore, with appropriate use of transparent components and/or appropriate positioning of openings, the filling level of such liquid tanks can be easily established by visual inspection.

The first line 112, the second line 113 and the delivery hose 117 are formed as one part, and are formed by a connecting hose 122 that is preferably formed in one piece. As a result, the number of connecting points is reduced, so that the risk of deposits forming is reduced.

Between the liquid tank 110 and the control electronics 108 is a detector 123 for identifying the liquid tank 110, the detector 123 being formed to detect information printed on the liquid tank or stored on the liquid tank and pass corresponding information on to the control electronics. As a result, the control electronics 108 are able to adapt various parameters, such as the level of the high voltage, the output of the pump, etc., to the liquid 103 to be sprayed. Particularly preferably, RFID markings, which are, in particular, formed such that they can be read and written, may be provided here, in order that current information, such as, for example, a date of the first use of the liquid tank, can also be stored.

In the embodiment represented, the atomizer 101 comprises 8 atomizer nozzles 102a to 102h, which are arranged in the manner of a ring (see FIG. 3). As a result, solid areas of several square centimeters can be sprayed, so that it is ensured that spraying makes rapid progress.

The atomizer nozzles 102a to 102h form a nozzle array 124 (see FIG. 3), the nozzle array 124 being formed as a grid 125 with grid lines 127a to 127f crossing at grid points 126a to 126i, it being provided, in particular, that the atomizer nozzles 102a to 102h form grid points of parallel grid lines. Such a regular geometrical arrangement allows a more uniform application of the liquid to be achieved.

It is also evident from FIGS. 1 and 2 that the housing 101 comprises a grip portion 128, a head portion 129 and a middle portion 130 arranged between the grip portion 128 and the head portion 129, the atomizer nozzles 102a to 102h being arranged in the head portion 129, the delivery device 111 being arranged between the liquid tank 110 and the atomizer nozzles 102a to 102h.

The control electronics comprise sensors S102-1 and S102-2, with which the voltage V102 and/or the current intensity A102 at the atomizer nozzle 102g are detected. Furthermore, the control electronics 108 comprise sensors S109-1 and S109-2, with which the voltage V109 and/or the current intensity A109 at the high-voltage source 109 are detected.

The delivery device 111 and/or the high-voltage source 109 are controlled in dependence on the voltage V102 and/or the current intensity A102 measured at the atomizer nozzle 102g and/or in dependence on the voltage V109 and/or the current intensity A109 measured at the high-voltage source 109 to optimize the dispensing of liquid by the atomizer 101. As a result, the proper functioning of the delivery device 111 and/or the high-voltage source 109 can be monitored. Furthermore, such monitoring allows improvement measures to be introduced, error messages to be output and quality to be monitored.

It is also envisaged to carry out an analysis of the current intensity A102 or A107 and/or the voltage V102 or V107 at at least one of the atomizer nozzles 102a to 102h and an electrically conductive portion of the operating element 107 of the activation mechanism 106 and to carry out a comparison of these measurements with reference values that are stored in the control electronics 108. As a result, the proper functioning of the atomizer can likewise be monitored. Such monitoring likewise allows improvement measures to be introduced, error messages to be output and quality to be monitored. The voltage and/or current intensity at the operating element 107 are measured by sensors S107-1 and S107-2.

It is also provided that, by an analysis of measured current intensities and/or voltages, a distance value AW between at least one of the atomizer nozzles 102a to 102h and a surface F to be sprayed is determined.

Furthermore, it is provided that, by an analysis of measured current intensities and/or the voltages, a coating parameter BP, such as, for example, a thickness of a layer on the surface F to be sprayed, is determined.

It is also provided that, by an analysis of measured current intensities and/or voltages of at least one of the atomizer nozzles 102a to 102h, an alignment of the at least one atomizer nozzle 102a to 102h with respect to the surface F to be sprayed is determined.

According to a variant of an embodiment that is not represented, it is provided that the atomizer comprises in addition to the first liquid tank a second liquid tank, that the atomizer comprises in addition to the first delivery device a second delivery device, that arranged between the delivery devices and the at least one atomizer nozzle is a mixing device, a delivery volume of the first delivery device and a delivery volume of the second delivery device being controlled in such a way that a mixed liquid of a prescribed composition is produced in the mixing device. As a result, different liquids can be mixed before spraying. By operating the delivery devices with different delivery outputs, the mixing ratio can also be determined.

As is evident from FIG. 1, it is also provided that the atomizer 101 comprises a heating device 140 and a cooling device 141, the liquid 103 being heated or cooled to achieve a prescribed temperature and/or viscosity before leaving the atomizer nozzles 102a to 102h.

It is provided that, when there is an activation of the atomizer 101, first the high-voltage generator 109 is activated and then the delivery device 111 is activated. It can be ensured in this way that liquid 103 arriving at the atomizer nozzles 102a to 102h is atomized immediately and the atomizer nozzles do not drip.

Furthermore, it is provided that, when there is a deactivation of the atomizer, first the delivery device is deactivated and then the high-voltage generator is deactivated. As a result, dripping of the atomizer nozzles can likewise be prevented. In addition, it is provided that, before its deactivation, the delivery device is automatically switched from forward delivery to brief backward delivery. As a result, the liquid is sucked out from the second line 113, so that dripping is avoided even more reliably and the time required for the switching-off operation can be reduced.

In the activating procedure, it is also provided that, when there is an activation of the atomizer 101 before an activation of the high-voltage generator 109, the atomizer nozzles 102a to 102h are brought from the inactive position R102 into the active position A102, the atomizer nozzles 102a to 102h being moved by the lifting cylinder 134 for this purpose.

In the deactivating procedure, it is also provided that, when there is an deactivation of the atomizer 101 after an deactivation of the high-voltage generator 109, the atomizer nozzles 102a to 102h are brought from the active position A102 into the inactive position R102, the atomizer nozzles 102a to 102h being moved again by the lifting cylinder 134 for this purpose.

Alternatively or in addition to movement of the atomizer nozzles, a housing part may also be formed as a slide (not represented), which is pushed in front of the atomizer nozzles to cover them in the deactivated state, and thereby preferably operates an on-off switch.

LIST OF DESIGNATIONS

101 Atomizer (first variant)
102a-102h Atomizer nozzle
103 Liquids
104 Housing
105 Energy source
106 Activation mechanism (electrical button or electronic contact)
107 Electrical button
107a Actuating element of 107
108 Control electronics
109 High-voltage source
110 Liquid tank
110a Film bag
111 Delivery device
112 First line
113 Second line
114 Pump
115 Suction pump
116 Hose pump
117 Delivery hose
116a Rotor
116b, 116c Roller
117 Delivery hose
118 Switching device
119 Signal transmitter
120 Connection mechanism
121 Valve
122 Connecting hose
123 Detector for identifying the liquid tank
124 Nozzle array
125 Grid
126a-126i Grid point
127a-127f Grid line
128 Grip portion
129 Head portion
130 Middle portion
131 Interior space
132 Outer side
133 Baseplate
134 Lifting cylinder
140 Heating device
141 Cooling device
AW Distance value
BP Coating parameter
F Surface to be coated
S102-1, S102-2 Sensor on 102g
S107-1, S107-2 Sensor on 107
S109-1, S109-2 Sensor on 109

The invention claimed is:
1. A method for controlling an electrostatic atomizer for liquids, the atomizer comprising a liquid tank and a delivery device for liquid from the liquid tank, a high-voltage source and a plurality of atomizer nozzles for the atomization of liquid, the plurality of atomizer nozzles are arranged in a rectangular geometrical ring arrangement, which is formed of elongated grid lines extending in parallel directions that form a plurality of columns that are arranged next to one another and grid lines extending in parallel directions that form a plurality of rows that are arranged below one another, with the elongated grid lines and the grid lines crossing at points, respectively, thereby forming a grid of parallel grid lines including grid points on outermost grid lines of the rectangular geometrical ring arrangement, such that the plurality of atomizer nozzles are arranged only at the grid points on the outermost grid lines of the rectangular geometrical ring arrangement, with at least one of the atomizer nozzles being connected to the high-voltage source, wherein a voltage and a current intensity at the at least one of the atomizer nozzles are detected by sensors of control electronics and/or wherein a voltage and a current intensity at the high-voltage source are detected by sensors of the control electronics.

2. The method as claimed in claim 1, wherein the atomizer comprises:
   a housing,
   an electrical energy source, by which the high-voltage source is supplied,
   an activation mechanism, by which the atomizer is activated, and
   the control electronics, by which the dispensing of liquid by the atomizer is controlled.

3. The method as claimed in claim 2, wherein an analysis of the current intensity and the voltage at the at least one of the atomizer nozzles and an electrically conductive portion of the housing or of an operating element of the activation mechanism is performed and a comparison of these measurements with reference values is carried out.

4. The method as claimed in claim 3, wherein by an analysis of measured current intensities and voltages, a distance value between the at least one of the atomizer nozzles and a surface to be sprayed is determined.

5. The method as claimed in claim 3, wherein by an analysis of measured current intensities and voltages, a coating parameter of a surface to be sprayed is determined.

6. The method as claimed in claim 1,
   wherein the delivery device is arranged between the liquid tank and the at least one of the atomizer nozzles,
   the delivery device being connected to the liquid tank by a first line and liquid being sucked out of the liquid tank by the delivery device, and
   the delivery device being connected to the at least one of the atomizer nozzles by a second line and liquid being delivered by the delivery device to the at least one of the atomizer nozzles,
   the first line and the second line being formed as a hose extruded in one piece.

7. The method as claimed in claim 6, wherein the delivery device and/or the high-voltage source are controlled, in a closed-loop manner, in dependence on the voltage and the current intensity measured at the at least one of the atomizer nozzles and/or in dependence on the voltage and the current intensity measured at the high-voltage source to optimize the dispensing of liquid by the atomizer.

8. The method as claimed in claim 1, wherein by an analysis of measured current intensities and voltages of the at least one of the atomizer nozzles, an alignment of the at least one of the atomizer nozzles with respect to a surface to be sprayed is determined.

9. The method as claimed in claim 1, wherein the atomizer comprises in addition to the first liquid tank a second liquid tank, wherein the atomizer comprises in addition to the first delivery device a second delivery device, in that arranged between the delivery devices and the at least one of the atomizer nozzles is a mixing device, a delivery volume of the first delivery device and a delivery volume of the second delivery device being controlled in such a way that a mixed liquid of a prescribed composition is produced in the mixing device.

10. The method as claimed in claim 1, wherein the atomizer comprises a heating device and/or a cooling device, the liquid being heated or cooled to achieve a prescribed temperature and/or viscosity before leaving the at least one of the atomizer nozzles.

11. The method as claimed in claim 1, wherein, when there is an activation of the atomizer, first the high-voltage source generator is activated and then the delivery device is activated.

12. The method as claimed in claim 11, wherein, when there is an activation of the atomizer before an activation of the high-voltage generator, the at least one of the atomizer nozzles is brought from an inactive position into an active position, the at least one of the atomizer nozzles and/or the housing being moved for this purpose and/or at least one housing portion, as a slide, being moved in relation to the at least one of the atomizer nozzles.

13. The method as claimed in claim 11, wherein, when there is a deactivation of the atomizer after a deactivation of the high-voltage source generator, the at least one of the atomizer nozzles is brought from an active position into an inactive position, the at least one of the atomizer nozzles and/or the housing, at least one housing portion, being moved for this purpose.

14. The method as claimed in claim 1, wherein, when there is a deactivation of the atomizer, first the delivery device is deactivated and then the high-voltage source generator is deactivated, it being provided that, before its deactivation, the delivery device is automatically switched from forward delivery to brief backward delivery.

* * * * *